United States Patent [19]

Dumas et al.

[11] Patent Number: 4,904,520
[45] Date of Patent: Feb. 27, 1990

[54] GAS-PERMEABLE, LIQUID-IMPERMEABLE NONWOVEN MATERIAL

[75] Inventors: David H. Dumas; Elliott Echt, both of Wilmington, Del.

[73] Assignee: Hercules Incorporated, Wilmington, Del.

[21] Appl. No.: 258,913

[22] Filed: Oct. 17, 1988

[51] Int. Cl.$^4$ .................... A61F 13/00; B01D 39/16; B32B 5/32; D21H 1/08; D21H 5/20

[52] U.S. Cl. .................... 428/212; 128/849; 162/146; 162/149; 162/207; 206/438; 206/439; 206/524.2; 206/524.6; 206/811; 220/449; 220/453; 220/DIG. 11; 229/3.1; 229/3.5 R; 428/286; 428/288; 428/296; 428/297; 428/302; 428/311.5; 428/315.5; 428/315.9

[58] Field of Search ............ 162/146, 149, 207; 428/212, 286, 288, 296, 297, 302, 311.5, 315.5, 315.9

[56] References Cited

U.S. PATENT DOCUMENTS

| | | | |
|---|---|---|---|
| 3,158,532 | 11/1964 | Pall et al. | 162/146 |
| 3,808,094 | 4/1974 | McKnight | 162/146 |
| 4,084,949 | 4/1978 | Biggias | 162/146 |
| 4,154,883 | 5/1979 | Elias | 162/149 |
| 4,196,245 | 4/1980 | Kitson et al. | 428/198 |
| 4,210,487 | 7/1980 | Driscoll | 162/149 |
| 4,264,691 | 4/1981 | O'Rell et al. | 429/250 |
| 4,330,602 | 5/1982 | O'Rell et al. | 429/206 |
| 4,341,216 | 7/1982 | Obemour | 128/287 |
| 4,508,113 | 4/1985 | Maloney | 428/296 |
| 4,645,565 | 2/1987 | Vallee et al. | 162/146 |
| 4,657,804 | 4/1987 | Mays et al. | 428/212 |
| 4,728,394 | 3/1988 | Shinjou et al. | 162/207 |
| 4,818,340 | 4/1989 | Hasegawa et al. | 162/146 |

FOREIGN PATENT DOCUMENTS

2095616 10/1982 United Kingdom .

Primary Examiner—James C. Cannon
Attorney, Agent, or Firm—Joanne W. Patterson

[57] ABSTRACT

Disclosed is a liquid-impermeable, gas-permeable nonwoven material comprising a thermally consolidated blend of (1) 5% to 30% of a first polyolefin pulp, (2) 15% to 90% of a second polyolefin pulp having a melting point at least 20° C. higher than the first polyolefin pulp, and (3) 5% to 55% of a staple fiber. Also disclosed is a wet forming method for making such a nonwoven material without the use of surfactants.

24 Claims, No Drawings

GAS-PERMEABLE, LIQUID-IMPERMEABLE NONWOVEN MATERIAL

FIELD OF THE INVENTION

This invention relates to a gas-permeable, liquid-impermeable nonwoven material as well as laminates prepared from such a material. This invention also relates to a wet forming method for making such a nonwoven material without the use of surfactants.

BACKGROUND OF THE INVENTION

In many medical applications there is a need for a wrapping or covering material that is resistant to penetration of fluids containing bacterial contamination, but is also permeable to gases. Gas permeability is desirable, for example, to permit the infusion of a gas such as steam or ethylene oxide for sterilization, or to permit the passage of air and water vapor when the material is used as a drape for covering patients or for making surgical gowns. There is also a need for liquid-impermeable, gas-permeable materials for nonmedical applications such as protective clothing.

In designing such a material, it is difficult to prevent the penetration of liquids without making the material insufficiently permeable to air. Various methods involving the use of a water-repellent surface treatment or lamination of several layers have been proposed to achieve the desired combination of properties. A water-impervious, gas-permeable laminated material comprising a ply of hydrophobic, microfine fibers produced by a dry forming, melt blown process, fuse-bonded to a layer of conjugate fibers having a low melting sheath and a high melting core is described in U.S. Pat. No. 4,657,804 (Mays et al.). This material is impregnated with a water-repellent binder and treated with a water-repellent finish. U.S. Pat. No. 4,196,245 (Kilson et al.) discloses a composite nonwoven fabric comprising at least two adjacent hydrophobic plies of microfine fibers produced by a dry forming, melt blown process, and one air-permeable, nonwoven cover ply. GB 2,095,616 describes a liquid-impermeable, water vapor-permeable material comprising a layer of absorbent nonwoven fabric that is free of any surface-active component and a layer of water-repellent nonwoven fabric, which may be treated with a water-repellent finish. The layers are attached to one another by means of a discontinuous layer of hydrophobic material.

A material that can be produced by a wet forming process and provide resistance to penetration of liquids containing bacterial contamination and that is also gas-permeable, without requiring a water-repellent surface treatment or lamination to other materials, would be an improvement over presently available materials.

SUMMARY OF THE INVENTION

It has now been found that a nonwoven material that is air-permeable and hydrophobic and that can be thermally bonded to other materials without the use of adhesives can be produced by a wet forming process. The nonwoven material of this invention comprises a thermally consolidated blend comprising (1) from about 5% to about 30% of a first polyolefin pulp, (2) from about 15% to about 90% of a second polyolefin pulp having a melting point at least 20° C. higher than the first polyolefin pulp, and (3) from about 5% to about 55% of a staple fiber, based on the total weight of the blend, said material being impermeable to liquids and permeable to gases. Optionally, 0.5% to 20% wood pulp can be added.

DETAILED DESCRIPTION OF THE INVENTION

The thermally consolidated, liquid-impermeable material of this invention includes from about 5% to about 30% of a first polyolefin pulp and from about 15% to about 90%, based on the total weight of the material, of a second polyolefin pulp that melts at a temperature at least 20° C. higher than the first pulp. About 20% of the lower melting polyolefin pulp and about 40% of the higher melting polyolefin pulp are preferred. Polyolefin pulps are well known in the art. For example, see "Pulp, Synthetic," Kirk-Othmer, *Encyclopedia of Chemical Technology*, 3rd Ed. (New York 1982), Vol. 19, pp. 420–435. These pulps are very fine, highly branched, discontinuous fibrils made from thermoplastic polymers. Their visual appearance and dimensions closely resemble those of wood pulp. The polyolefin pulps provide liquid barrier properties without the need for water repellent surface treatments or lamination to other materials. The polyolefin pulps also make it possible to bond the liquid-impermeable material to other materials without the use of adhesives, for example, by thermal or ultrasonic bonding.

Representative of the polymers from which the polyolefin pulps are made are polyethylene, polypropylene, poly(4-methylpentene-1), copolymers of ethylene and propylene, and copolymers of ethylene or propylene and other 1-olefins such as 1-butene and 1-hexene. The polyolefin pulps can be composed solely of one of these polymers, or they can be composed of mixtures of two or more of the polymers. The preferred lower melting polyolefin pulp is polyethylene pulp and the preferred higher melting polyolefin pulp is polypropylene pulp.

The liquid-impermeable material also comprises from about 5% to about 55% of a staple fiber to impart the desired gas permeability to the finished product. The staple fiber also provides sheet strength, especially before the material is dried and thermally consolidated. Fibers having a length of 5–10 mm are preferred for wet forming. The air permeability desired will vary with the end use of the product, e.g., a material used in the manufacture of a garment would have to be more gas-permeable than a material used for packaging surgical supplies. Any intrinsically hydrophobic staple fiber can be used, for example, fibers of polypropylene; polyethylene; ethylene/propylene copolymers; polyester; acrylic; copolymers of ethylene and other 1-olefins such as butene, hexene, octene, or 4-methylpentene-1; and fibers made from more than one of these polymers, e.g., a bicomponent polyester/polypropylene, polyester/polyethylene, or polyethylene/polypropylene fiber. Polypropylene staple fibers are preferred.

The thermally consolidated, liquid-impermeable material of this invention can optionally include from about 0.5% to about 20% of wood pulp to provide additional wet web strength. The amount of wood pulp used must be such that the liquid barrier properties of the product are not adversely affected.

Nothing other than the blend of polyolefin pulps and the staple fiber is needed to produce the required combination of properties in the final product, namely, impermeability to liquids and permeability to gases. The liquid impermeability of the material of this invention is indicated by a Mason Jar test value of at least 60 minutes (INDA test method 80.7). The material also has a Frazier air permeability of at least 10 cubic feet per minute (cfm)/sq. ft. (ASTM test method D-737). Air permeability is used as a measure of the comfort of a person covered by the material, as well as a measure of how well a sterilizing gas will pass through the material.

The liquid-impermeable material of this invention is made by a wet forming process. The synthetic pulps, and optionally the wood pulp, are first dispersed in water at high shear. Dispersed staple fibers are then added. The solids are adjusted to a level low enough to maintain a good dispersion. The level of solids will vary depending on the adequacy of the agitation in a particular system. The dispersion of pulps and staple fibers is then formed into a sheet, pressed, dried to remove the water, and heated to a temperature sufficient to melt the lower melting synthetic pulp. The fusion of the lower melting synthetic pulp binds the blend of fibers together and increases the strength of the finished product.

A good dispersion of synthetic pulp and staple fiber in water is essential to form a uniform wet-laid sheet. However, adding surfactants to the water must be avoided in the process of this invention, since this will render the sheet hydrophilic. Eliminating surfactants also helps to improve wet web strength and thus makes lower basis weights possible. Low basis weight materials drape and fold more easily than high basis weight materials and are less expensive. The synthetic pulp can be adequately dispersed by adding at least one water-soluble polymer to the water. Suitable water-soluble polymers include anionic acrylamide copolymers, hydroxypropylguar and mixtures thereof. A combination of an anionic acrylamide copolymer and hydroxypropylguar is preferred. The hydroxypropylguar can be added dry during the high shear aqueous dispersion of the synthetic pulps or as a solution after the synthetic pulps are dispersed in water. A solution of the acrylamide copolymer is added after the high shear dispersing step. A preferred method of adding the combination of the two water-soluble polymers comprises adding hydroxypropylguar at a level of from about 10 ppm to about 75 ppm to the dispersing equipment and adding from about 7 ppm to about 50 ppm of the acrylamide copolymer to the forming section of the paper machine.

It may be desirable to bond other fabrics to one or both sides of the liquid-impermeable material of this invention to enhance properties other than liquid impermeability and gas permeability, e.g., additional strength or softness. Suitable materials that can be bonded to the liquid-impermeable material include woven fabrics and fabrics produced by conventional nonwoven processes such as spunbonded, needled, carded or hydroentangled nonwovens. If another material is bonded to both sides of the liquid-impermeable material, the same material can be bonded to both sides or a different material can be bonded to each side. For example, a composite fabric can be prepared by bonding a layer of spun bonded material to one side of the liquid-impermeable material to give additional strength, and bonding a carded staple fiber layer to the other side for improved softness and drapability.

All percentages in this specification are by weight unless otherwise noted.

EXAMPLE 1

This example describes the preparation of a wet-laid nonwoven material having the following composition:

40% PULPEX ® P-AD polyolefin pulp (Hercules Incorporated)
20% PULPEX ® E-A polyolefin pulp (Hercules Incorporated)
40% HERCULON ® T-153 polypropylene staple fiber, 2.2 denier with a length of 10 millimeters (Hercules Incorporated)

The PULPEX ® E-A, which is a polyethylene pulp, and PULPEX ® P-AD, which is a polypropylene pulp, are opened separately in a disc refiner, and then pumped to the machine chest of a Fourdrinier type paper machine. The staple fiber is added to the machine chest and the solids in the machine chest are adjusted to 0.25%. A solution of GENDRIV 492SP hydroxypropyl guar gum (Aqualon Company) is added to the machine chest at a level of 75 ppm in the liquid.

The dispersion of pulps and staple fibers is provided to the forming section of a paper machine to which is added sufficient RETEN ® 523P anionic acrylamide copolymer (Hercules Incorporated) to give a level of about 10 ppm in the low consistency forming section. The consistency at the slice of the flow spreader is 0.08%.

The nonwoven that is formed has a basis weight of 0.9 ounce per square yard. The material is partially fused by passing each side against a drum coated with a nonstick material and having a surface temperature of 123° C. The resulting product has a density of 0.31 g/cc and a Frazier air permeability of 46.3 cfm/sq. ft. The product has a Mason Jar test result of more than 60 minutes before there is any penetration by a 1% sodium chloride solution.

EXAMPLE 2

This example describes the preparation of a wet-laid, nonwoven material having the following composition:

10% bleached softwood kraft wood pulp refined to 500 Canadian Standard Freeness (CSF)
10% PULPEX ® E-A polyolefin pulp (Hercules Incorporated)
40% PULPEX ® P-AD polyolefin pulp (Hercules Incorporated)
40% HERCULON ® T-153 polypropylene staple fiber, 2.2 denier with a fiber length of 5 millimeters (Hercules Incorporated)

The forming method described in Example 1 is used, including the use of hydroxypropylguar and the acrylamide copolymer in the amounts specified.

The dispersion of fibers is formed into a nonwoven material with a 1 ounce per square yard basis weight and treated in one of the following ways:

(a) The material is densified between two steel rolls loaded pneumatically and heated to 121° C. The product has a Frazier air permeability (ASTM test method D-737) of 2.2 cfm/sq. ft.

(b) The material is densified in a laminator consisting of a rubber blanket held against a heated steel drum by 50 psi air pressure, with a drum surface temperature of 149° C. The resulting product has a density of 0.47 g/cc. and a Frazier air permeability of 4.5 cfm/sq. ft.

(c) The material is partially fused by passing each side against a drum coated with a nonstick material and having a surface temperature of 123° C. The resulting product has a density of 0.28 g/cc and a Frazier air permeability of 15.1 cfm/sq. ft.

Samples a and c are tested by the Mason Jar test (INDA Test Method 80.7) and resisted penetration of 1% sodium chloride solution for over 60 minutes.

EXAMPLE 3

This example describes the preparation of a wet-laid, nonwoven material having the following composition:
40% PULPEX® P-AD polyolefin pulp (Hercules Incorporated)
20% PULPEX® E-A polyolefin pulp (Hercules Incorporated)
35% HERCULON® T-153 polypropylene fiber (2.2 denier, 5 mm) (Hercules Incorporated)
5% HERCULON® T-153 polypropylene fiber (2.2 denier, 10 mm) (Hercules Incorporated)

The forming method described in Example 1 is used, including the use of hydroxypropylguar and the acrylamide copolymer in the amounts specified.

When fused on a drum dryer having a non-stick surface, the resulting nonwoven material has a basis weight of 39 grams per square meter (gsm), a density of 0.26 g/cc, a Frazier air permeability of 36.3 cfm/sq. ft., a Mason Jar test value of greater than 60 minutes and a machine direction tensile strength of 2.3 lb/in.

EXAMPLE 4

The nonwoven material prepared as described in Example 3 is placed on a layer of 9 gsm unbonded carded polypropylene staple fiber, and an additional 9 gsm of polypropylene staple is carded onto the top of the nonwoven material. The three layers are passed through a point bonding calender heated internally to 138° C. The resulting three layer laminate has a basis weight of 57 gsm, a density of 0.22 g/cc, a Frazier air permeability of 39 cfm/sq. ft., a Mason Jar test value of greater than 60 minutes and a machine direction tensile strength of 3.8 lb/in.

What we claim and desire to protect by Letters Patent is:

1. A nonwoven material comprising a thermally consolidated, wet laid blend comprising (1) from about 5% to about 30% of a first polyolefin pulp, (2) from about 15% to about 90% of a second polyolefin pulp having a melting point at least 20° C. higher than the first polyolefin pulp, and (3) from about 5% to about 55% of a staple fiber, based on the total weight of the blend, said material being impermeable to liquids and permeable to gases.

2. The material of claim 1 which additionally comprises from about 0.5% to about 20% of wood pulp.

3. The material of claim 1 wherein the first polyolefin pulp is polyethylene pulp and the second polyolefin pulp is polypropylene pulp.

4. The material of claim 1 wherein the staple fiber is polypropylene staple fiber.

5. The material of claim 3 wherein the staple fiber is polypropylene staple fiber.

6. A wet forming process for the preparation of a nonwoven material comprising
(1) dispersing in water a mixture comprising (a) from about 5% to about 30% of a first polyolefin pulp, (b) from about 15% to about 90% of a second polyolefin pulp having a melting point at least 20° C. higher than the first polyolefin pulp, and (c) from about 5% to about 55% of a staple fiber, based on the total weight of the material, in the presence of at least one water-soluble polymer and in the absence of a surface active agent,
(2) forming a sheet from the aqueous dispersion,
(3) drying, and
(4) heating the sheet to a temperature sufficient to melt the first polyolefin pulp, said nonwoven material being impermeable to liquids and permeable to gases.

7. The process of claim 6 wherein the mixture of step (1) additionally comprises from about 0.5% to about 20% wood pulp.

8. The process of claim 6 wherein the first polyolefin pulp is polyethylene pulp and the second polyolefin pulp is polypropylene pulp.

9. The process of claim 6 wherein the staple fiber is polypropylene staple fiber.

10. The process of claim 8 wherein the staple fiber is polypropylene staple fiber.

11. The process of claim 6 wherein the water-soluble polymer is a combination of an anionic acrylamide copolymer and hydroxypropylguar.

12. The product made by the process of claim 6.

13. The product made by the process of claim 7.

14. A process for preventing the passage of liquids to an object while allowing the passage of gases comprising covering the object with a nonwoven material comprising a thermally consolidated, wet laid blend comprising:
(1) from about 5% to about 30% of a first polyolefin pulp,
(2) from about 15% to about 90% of a second polyolefin pulp having a melting point at least 20° C. higher than the first polyolefin pulp, and
(3) from about 5% to about 55% of a staple fiber, based on the total weight of the blend.

15. The process of claim 14 wherein the thermally consolidated blend additionally comprises from about 0.5% to about 20% wood pulp.

16. The process of claim 14 wherein the first polyolefin pulp is polyethylene pulp and the second polyolefin pulp is polypropylene pulp.

17. The process of claim 14 wherein the staple fiber is polypropylene staple fiber.

18. The process of claim 16 wherein the staple fiber is polypropylene staple fiber.

19. A laminate comprising a first layer and a second layer, said second layer comprising a thermally consolidated, wet laid blend comprising
(1) for about 5% to about 30% of a first polyolefin pulp,
(2) from about 15% to about 90% of a second polyolefin pulp having a melting point at least 20° C. higher than the first polyolefin pulp, and
(3) from about 5% to about 55% of a staple fiber, based on the total weight of the blend,
said laminate being impermeable to liquids and permeable to gases.

20. The laminate of claim 19 wherein the thermally consolidated blend additionally comprises form about 0.5% to about 20% wood pulp.

21. The laminate of claim 19 wherein said second layer comprises a consolidated blend of polyethylene pulp, polypropylene pulp and polypropylene staple fiber.

22. The laminate of claim 19 which additionally comprises a third layer adjacent to the second layer.

23. The laminate of claim 22 wherein the first and third layers comprise carded polypropylene staple fiber.

24. The laminate of claim 20 which additionally comprises a third layer adjacent to the second layer.

* * * * *